United States Patent [19]

Carrico et al.

[11] 4,171,432

[45] Oct. 16, 1979

[54] FLAVIN ADENINE DINUCLEOTIDE-IODOTHYRONINE CONJUGATES

[75] Inventors: Robert J. Carrico; Richard D. Johnson, both of Elkhart, Ind.

[73] Assignee: Miles Laboratories, Inc., Elkhart, Ind.

[21] Appl. No.: 917,962

[22] Filed: Jun. 22, 1978

[51] Int. Cl.² ............................................. C07H 19/16
[52] U.S. Cl. ........................................ 536/26; 435/7; 536/24; 536/27; 536/28
[58] Field of Search ....................... 536/27, 26, 28, 29, 536/24; 195/103.5 A, 63, 103.5 R

[56] References Cited

U.S. PATENT DOCUMENTS

| | | | |
|---|---|---|---|
| 3,590,029 | 6/1971 | Koch | 536/26 |
| 3,983,104 | 9/1976 | Vorbruggen | 536/24 |
| 4,040,907 | 8/1977 | Ullman et al. | 195/103.5 R |
| 4,043,872 | 8/1977 | Blakemore et al. | 195/103.5 A |

*Primary Examiner*—Johnnie R. Brown
*Assistant Examiner*—Blondel Hazel
*Attorney, Agent, or Firm*—Andrew L. Klawitter

[57] ABSTRACT

Conjugates of the formula:

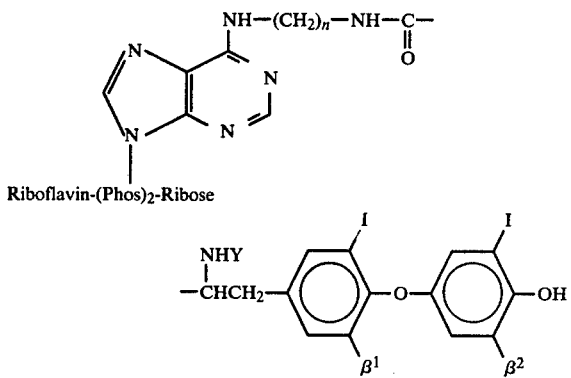

wherein Riboflavin-(Phos)₂-Ribose represents the riboflavin-pyrophosphate-ribose residue in flavin adenine dinucleotide (FAD), n equals 2 through 6, Y is hydrogen or trifluoroacetyl, and $\beta^1$ and $\beta^2$ are, independently, hydrogen or iodine; and intermediates in the synthesis of such FAD conjugates. The FAD-iodothyronine conjugates, particularly where the iodothyronine is thyroxine, are useful as labeled conjugates in specific binding assays for determining the iodothyronine in liquid media such as serum.

3 Claims, No Drawings

FLAVIN ADENINE DINUCLEOTIDE-IODOTHYRONINE CONJUGATES

BACKGROUND OF THE INVENTION

1. Field of the Invention

This invention relates to novel labeled conjugates for use in specific binding assays for an iodothyronine, particularly a thyroid hormone such as thyroxine, in a liquid medium such as serum.

The iodothyronines have the following general formula:

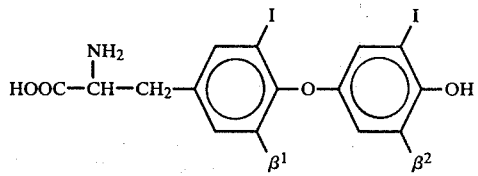

wherein $\beta^1$ and $\beta^2$ are, independently, hydrogen or iodine. The principal iodothyronines of clinical interest are listed in Table 1 below.

TABLE 1

| Iodothyronine | $\beta^1$ | $\beta^2$ |
| --- | --- | --- |
| 3,5,3',5'-tetraiodothyronine (thyroxine; T-4) | iodine | iodine |
| 3,5,3'-triiodothyronine (liothyronine; T-3) | iodine | hydrogen |
| 3,3',5'-triiodothyronine ("reverse" T-3) | hydrogen | iodine |
| 3,3'-diiodothyronine | hydrogen | hydrogen |

The quantitative determination of the concentration of the various iodothyronines, particularly the hormones T-3 and T-4, in serum and of the degree of saturation of the iodothyronine binding sites on the carrier protein thyroid binding globulin (TBG) are valuable aids in the diagnosis of the thyroid disorders.

2. Brief Description of the Prior Art

Various methodologies exist for the determination of iodothyronine concentrations in serum. A significant advance in iodothyronine assays was the development of the competitive protein binding assay by Murphy and Pattee, *J. Clin. Endocrinol. Metab.* 24:187(1964) in which radiolabeled iodothyronine competes with serum iodothyronine for binding to TBG. The development of specific antiserum for the various iodothyronines permitted radioimmunoassays to be devised in which radiolabeled and serum iodothyronine compete for binding to antibodies rather than to TBG. In both the competitive protein binding assay and the radioimmunoassay for an iodothyronine, the radiolabeled material consists of the native iodothyronine in which one or more of the iodine atoms are replaced by a radioactive iodine isotope, usually $^{125}I$.

Recently there have been developed non-radioisotopic specific binding assays which are applicable to the detection of various ligands including the iodothyronines. U.S. Pat. Nos. 4,043,872 and 4,040,907 describe a homogeneous enzyme-labeled binding assay for thyroxine and the enzyme-labeled thyroxine conjugate used therein. Other non-radioisotopic binding assays are described in German Offenlegungschriften Nos. 2,618,419 and 2,618,511 based on U.S. Ser. Nos. 667,982 and 667,996, filed on Mar. 18, 1976, and assigned to the present assignee, involving the use of particularly unique labeling substances, including coenzymes (e.g., FAD), chemiluminescent molecules, cyclic reactants, and cleavable fluorescent enzyme substrates. A further improvement in non-radioisotopic binding assays is offered in the U.S. patent application filed on even date herewith entitled "Specific Binding Assay with a Prosthetic Group as a Label Component" Ser. No. 917,961 and assigned to the present assignee, describing the use of organic prosthetic groups such as FAD as labeling substances in binding assays.

SUMMARY OF THE INVENTION

Novel flavin adenine dinucleotide-iodothyronine conjugates have been devised for use in binding assays for determining iodothyronines, and particularly in the assay referred to hereinbefore employing a prosthetic group label. The FAD-labeled iodothyronine conjugates have the general formula:

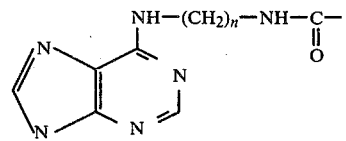

Riboflavin-(Phos)$_2$-Ribose

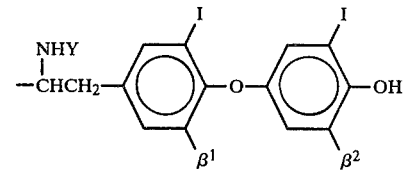

wherein Riboflavin—Phos)$_2$ Ribose represents the riboflavin-pyrophosphate-ribose residue in FAD; n equals 2 through 6, and preferably is 2 or 6; Y is hydrogen or trifluoroacetyl; and $\beta^1$ and $\beta^2$ are, independently, hydrogen or iodine, and preferably both are iodine.

The FAD-iodothyronine conjugates are used as labeled conjugates in binding assays for iodothyronines and are determined, i.e., monitored, for the purposes of the assay by measuring FAD activity, e.g., the coenzyme or prosthetic group activity of the labeled conjugate. Preferably the FAD-labeled conjugates are monitored by measuring holoenzyme activity generated upon combination of such conjugate with an apoenzyme that requires FAD to perform its catalytic function.

Preparation of the FAD-iodothyronine conjugates proceeds according to the following general reaction procedure:

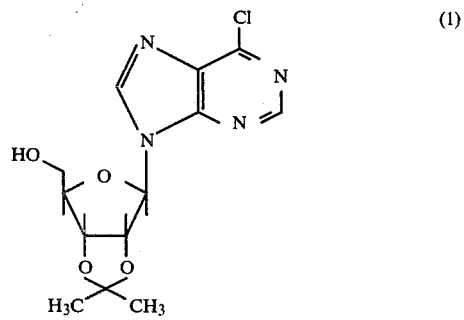

(1)

Reaction of 6-chloro-9-(2′,3′-O-isopropylidine-β-D-ribofuranosyl) purine (1) [Hampton, et al, J. Am. Chem. Soc. 83:150(1961)] with an α,ω-diaminoalkane selected from those listed in Table 2 yields the intermediate 6-(ω-aminoalkyl)-9-(2′,3′-O-isopropylidine-β-D-ribofuranosyl) purine (2).

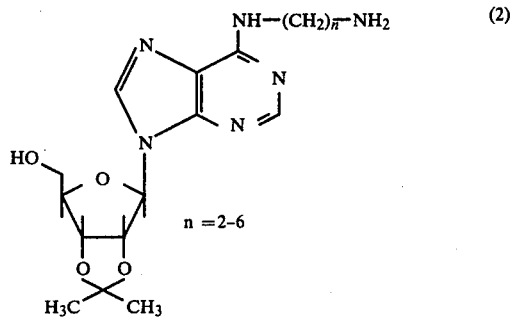

(2)

n = 2–6

TABLE 2

| η | α,ω-diaminoalkane |
|---|---|
| 2 | 1,2-diaminoethane |
| 3 | 1,3-diaminopropane |
| 4 | 1,4-diaminobutane |
| 5 | 1,5-diaminopentane |

TABLE 2-continued

| η | α,ω-diaminoalkane |
|---|---|
| 6 | 1,6-diaminohexane |

Treatment of the desired iodothyronine with trifluoroacetic acid yields the amine-protected iodothyronine intermediate (3).

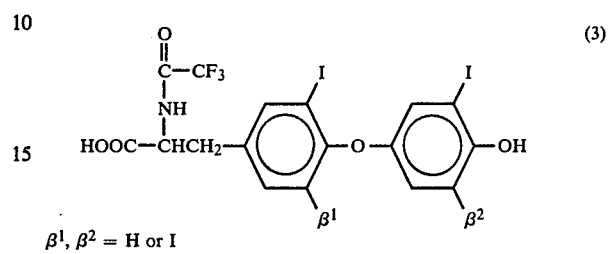

(3)

$\beta^1, \beta^2$ = H or I which reacts with the purine intermediate (2) in the presence of diphenylphosphoryl azide through formation of a peptide bond to yield the iodothyronine substituted adenosine intermediate (4).

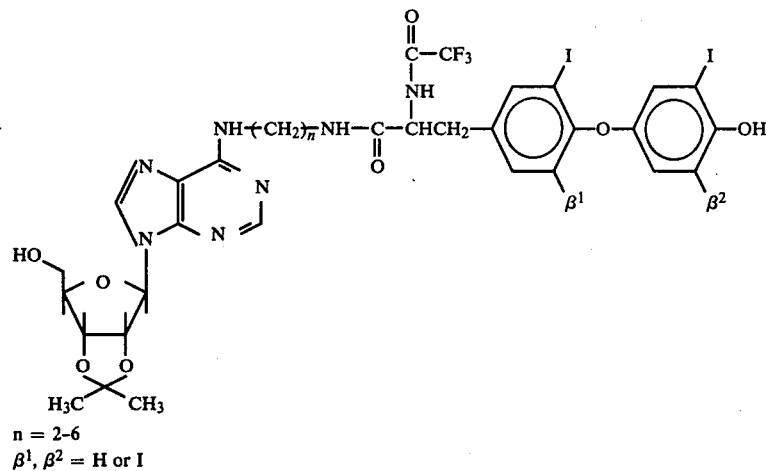

(4)

n = 2–6
$\beta^1, \beta^2$ = H or I

Treatment of intermediate (4) with phosphorous oxychloride produces the phosphorylated iodothyronine substituted adenosine intermediate (5).

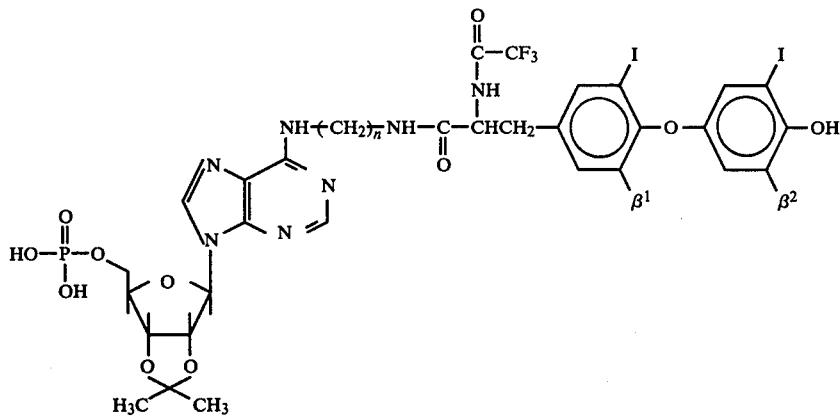

(5)

n = 2–6
$\beta^1, \beta^2$ = H or I which hydrolyzes in the presence of aqueous trifluoroacetic acid to generate the iodothyronine substituted 5'-adenylic acid intermediate (6).

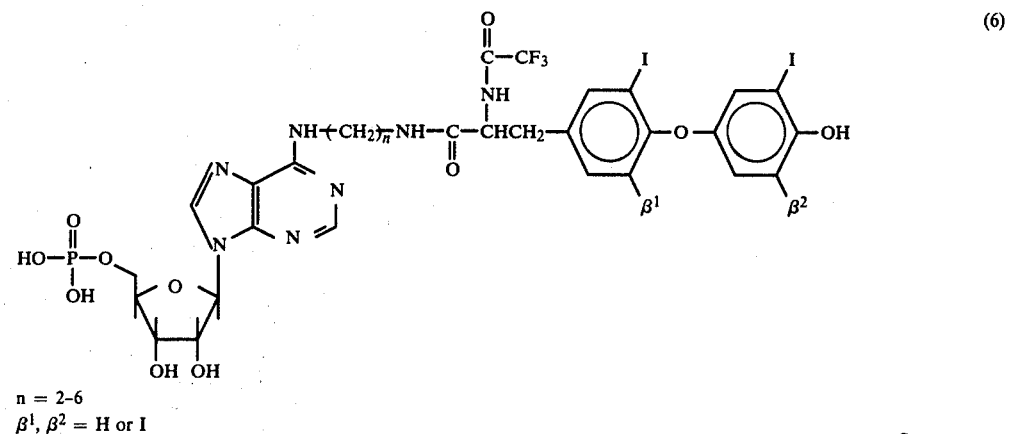

n = 2-6
$\beta^1, \beta^2$ = H or I

Condensation of riboflavin-5'-monophosphate with intermediate (6) activated to a phosphorimidazolidate by treatment with N,N'-carbonyldiimidazole yields FAD-labeled conjugates (7) wherein Y is a trifluoroacetyl radical, which with treatment with alkali to release the amine-protecting group yields FAD-labeled conjugates (7) wherein Y is hydrogen.

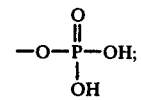

and $R^2$ and $R^3$ together form the group

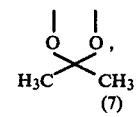

(7)

Riboflavin-(Phos)$_2$-Ribose
n = 2-6
$\beta^1, \beta^2$ = H or I

As illustrated above, the novel intermediate compounds (4-6) produced in the course of synthesizing the FAD-labeled conjugates have the following general formula:

or if $R^1$ is

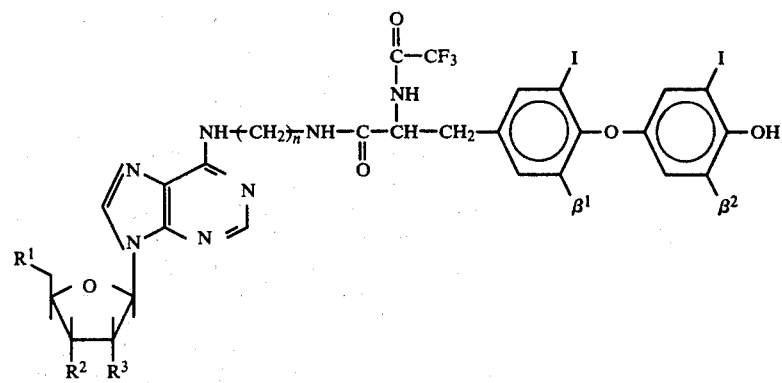

wherein n equals 2 through 6; $\beta^1$ and $\beta^2$ are, independently, hydrogen or iodine, $R^1$ is —OH or

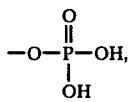

$R^2$ and $R^3$ are —OH.

The general reaction scheme described above is exemplified by the following descriptions of the synthesis of the ethyl (n=2) and hexyl (n=6) analogs of the FAD-labeled conjugates wherein the iodothyronine is thyroxine ($\beta^1$ and $\beta^2$=iodine). Also provided are descriptions of assay methods, and results therefrom, employing the exemplified analogs as labeled conjugates in a specific binding assay for thyroxine.

1. Ethyl Analog

1-I. PREPARATION OF THE LABELED CONJUGATE 6-(2-Aminoethyl)amino-9-(2',3'-O-isopropylidine-β-D-ribofuranosyl) purine (2)

13.56 grams (g) [41.5 millimoles (mmol)] of 6-chloro-9-(2',3'-O-isopropylidene-β-D-ribofuranosyl) purine (1) [Hampton et al, J. Am. Chem. Soc. 83:150(1961)] was added with stirring over a 15 minute period to a cold excess of 1,2-diaminoethane [75 milliliters (ml)]. The resulting solution was allowed to stand at room temperature for 24 hours. The solution was evaporated in vacuo and the resulting yellow oil was stirred with 50 ml of cold, saturated sodium bicarbonate. The mixture was evaporated in vacuo and the resulting residue was further repeatedly evaporated in vacuo first from water (3 times from 50 ml) and then from 2-propanol (4 times from 50 ml) to obtain a yellow glass (15 g). A portion (3 g) of the glass was dissolved in a small volume of water which was then applied to the top of a 25×55 centimeter (cm) Dowex 50W-X2 cation exchange column in the ammonium form (Bio-Rad Laboratories, Richmond, California USA).

The column was eluted with a linear gradient generated with 2 liters (L) each of water and 0.5 molar (M) ammonium bicarbonate. The elution was completed using a linear gradient generated with 2 L each of 0.5 M and 1 M ammonium bicarbonate. The effluent from the column was collected in 19 ml fractions and monitored by elution on silica gel thin layer chromatography (TLC) plates (E. Merck, Darmstadt, West Germany) with a 9:1 (v:v) mixture of ethanol and ammonium hydroxide. The developed TLC plates were examined under ultraviolet light, then sprayed with ninhydrin reagent [Randerath, Thin Layer Chromatography, Academic Press (1966)]. Fractions numbered 250 through 350 from the column chromatography were combined and evaporated in vacuo leaving the desired purine (2) as a pale yellow amorphous glass (1.5 g).

Analysis: Calculated for $C_{15}H_{22}N_6O_4$: C, 51.42; H, 6.33; N, 23.99. Found: C, 50.92; H, 6.54; N, 23.01

NMR (60 MHz, $CDCl_3$): δ 1.37 (s,3H, isopropylidene), 1.63 (s,3H, isopropylidene), 5.92 (d, 1H, 1'-ribose), 7.90 (s, 1H, purine), 8.26 (s, 1H, purine)

Optical Rotation $[\alpha]_D^{20} = -74.85°$ (c 1.0, $CH_3OH$).

The remaining crude product (12 g) was purified by chromatography on Dowex 50W-X2 as described above. The overall yield was 8 g (55%).

α-(N-Trifluoroacetyl)amino-β-[3,5-diiodo-4-(3',5'-diiodo-4'-hydroxyphenoxy)phenyl] propanoic acid (3)

This compound was prepared by the method of Blank, J. Pharm. Sci. 53:1333(1964). To a cooled (0° C.), stirred suspension of 5 g (6.4 mmol) of L-thyroxine (Sigma Chemical Co., St. Louis, Missouri USA) in 60 ml of dry ethyl acetate was added 11.5 ml of trifluoroacetic acid and 1.9 ml of trifluoroacetic anhydride. After 30 minutes the resulting clear solution was washed three times with 30 ml of water, once with 30 ml of 5% sodium bicarbonate, and twice with 50 ml of saturated sodium chloride. The combined aqueous washings were extracted twice with 20 ml of ethyl acetate. The ethyl acetate layers were combined and washed with 30 ml of water, then dried over magnesium sulfate. The dried ethyl acetate solution was evaporated in vacuo leaving a white solid. Recrystallization from a mixture of ethyl ether and petroleum ether gave a pinkish-white solid (3.95 g, 70.5% yield) having a melting point (m.p.) of 228°-230° C. with decomposition.

Analysis: Calculated for $C_{17}H_{10}F_3I_4NO_5$: C, 23.39; H, 1.15; N, 1.60. Found: C, 23.00; H, 1.05; N, 1.65

NMR [60 MHz, $DCON(CD_3)_2$] δ7.28 (s, 2H, aromatic), 8.03 (s, 2H, aromatic), 9.7 (m, 1H, amido).

IR (KCl): 1700 (>C=O)

Optical Rotation $[\alpha]_D^{25} = -14.97°$ (c 1.0 dimethylsulfoxide).

A second recrystallization produced a second precipitate (0.95 g) m.p. 224°-228° C. with decomposition. The overall yield was 87.5%.

N-{2-[N-(Trifluoroacetyl)-3,3',5,5'-tetraiodothyronyl] aminoethyl}-2',3'-O-isopropylidene adenosine (4)

A solution of 8.72 g (10.0 mmol) of α-(M-trifluoroacetyl) amino-β-[3,5-diiodo-4-(3',5'-diiodo-4'-hydroxyphenoxy)phenyl] propanoic acid (3) and 3.86 g (11.0 mmol) of 6-(2-aminoethyl) amino-9-(2',3'-O-isopropylidene-β-D-ribofuranosyl) purine (2) in 50 ml of dry dimethylacetamide was prepared under a dry argon atmosphere at −20° C. To this cold stirred solution was added a solution of 3.04 g (11.0 mmol) of diphenylphosphoryl azide (Aldrich Chemical Co., Milwaukee, Wisconsin USA) in 10 ml of dry dimethylacetamide followed by the addition of 1.6 ml (11.0 mmol) of dry triethylamine. The solution was left at room temperature for 22 hours. The solution was then added dropwise to 300 ml of cold (0° C.) water with stirring. The resulting white precipitate was collected by filtration and dried in vacuo (56° C.) to give 13.0 g of a light cream colored solid. The solid was dissolved in 500 ml of acetone and the solution was concentrated by boiling. The white solid which precipitated from the boiling acetone solution was collected by filtration while hot. Continued boiling of the filtrate produced two additional precipitates. The three precipitates were combined to give 8 g (66.6% yield) of a white solid, m.p. 198°-200° C. (decomposed).

Analysis: Calculated for $C_{32}H_{30}F_3I_4N_7O_8$: C, 31.89; H, 2.51; N, 8.14. Found: C, 31.95; H, 2.60; N, 7.86

NMR [220 MHz, $(CD_3)_2SO$] δ 1.32 (s, 3H, isopropylidene), 1.55 (s, 3H, isopropylidene), 6.14 (d, 1H, 1'-ribose), 7.02 (s, 2H, thyroxine), 7.82 (s, 2H, thyroxine), 8.25 (s, 1H, purine), 8.36 (s, 1H, purine), 8.41 (t, 1H, J=6, amido), 9.64 (d, 1H, J=8, trifluoroacetamido).

Optical Rotation $[\alpha]_D^{25} = -11.82°$ (c 1.0, pyridine).

N-{2-[N-(Trifluoroacetyl)-3,3',5,5'-tetraiodothyronyl]aminoethyl}-2',3'-O-isopropylidene-5'-adenylic acid monotriethylamine salt monohydrate (5)

A solution of 1.2 g (1.0 mmol) of N-{2-[N-(trifluoroacetyl)-3,3',5,5'-tetraiodothyronyl]aminoethyl}-2',3'-O-isopropylidene adenosine (4) in 10 ml of dry triethylphosphate was prepared under a dry argon atmosphere at 0° C. To the cold, stirred solution was added 0.45 ml (5 mmol) of phosphorous oxychloride. The resulting solution was kept for 24 hours at 0° C., then added dropwise with stirring to 1 L of ice water. The resulting precipitate was collected by filtration and dried in vacuo to give 1.23 g of a white solid. The solid was dissolved in acetone and 0.32 ml (2.2 mmol) of triethylamine was added. A precipitate formed. The mixture was evaporated in vacuo and the resulting residue lixiviated with dry acetone, then recrystalized from a mixture of dry methyl alcohol and dry ethyl ether to give 390 mg (27.8% yield) of a white solid, m.p. 173°–183° C. (decomposed).

Analysis: Calculated for $C_{38}H_{48}F_3I_4N_8O_{12}P$: C, 32.50; H, 3.45; N, 7.98. Found: C, 32.24; H, 3.08; N, 7.58

NMR [60 MHz, $(CD_3)_2SO$] δ 1.53 (s, 3H, isopropylidene), 6.2 (d, 1H, 1'H-ribose), 7.1 (s, 2H, thyroxine aromatic), 7.87 (s, 2H, thyroxine aromatic), 8.27 (s, 1H, purine), 8.52 (s, 1H, purine).

Optical Rotation $[\alpha]_D^{25} = -17.50°$ (c 1.0, $CH_3OH$).

N-{2-[N-(Trifluoroacetyl)-3,3',5,5'-tetraiodothyronyl]aminoethyl}-5'-adenylic acid (6)

200 milligrams (mg) (0.14 mmol) of N-{2-[N-(trifluoroacetyl-3,3',5,5'-tetraiodothyronyl]aminoethyl}-2',3'-O-isopropylidene-5'-adenylic acid monotriethylamine salt monohydrate (5) was suspended in 1 ml of water (0° C.) and trifluoroacetic acid (9 ml) was added dropwise with stirring. After 30 minutes a clear solution was obtained. The solution was kept cold (0° C.) for an additional 15 hours, then evaporated in vacuo (30° C.). The resulting residue was evaporated four times in vacuo (25° C.) from 20 ml volumes of anhydrous ethyl alcohol and then dried in vacuo (25° C.) leaving a white solid.

The solid was stirred for 30 minutes with 10 ml of cold methyl alcohol, then collected by filtration and dried in vacuo (25° C.) to give a white solid (135 mg, 76% yield) which slowly melted with decomposition above 188° C.

Analysis: Calculated for $C_{29}H_{27}F_3I_4N_7O_{11}P$: C, 27.97; H, 2.19; N, 7.87. Found: C, 28.11; H, 2.31; N, 7.65

NMR [220 MHz, $(CD_3)_2SO$] δ 5.95 (d, 1H, 1'-ribose), 7.04 (s, 2H, thyroxine aromatic), 7.84 (s, 2H, thyroxine aromatic), 8.25 (s, 1H, purine), 8.36 (s, 1H, purine), 8.43 (m, 1H, amido), 9.66 (d, 1H, trifluoroacetamido).

Optical Rotation $[\alpha]_D^{25} = -2.72°$ (c 1.0, pyridine).

Flavin adenine dinucleotide-thyroxine conjugate (7)

498 mg (0.4 mmol) of N-{2-[N-(trifluoroacetyl)-3,3',5,5'-tetraiodothyronyl]aminoethyl}-5'-adenylic acid (6) was dissolved in 10 ml of dry dimethylformamide and tri-n-butylamine [96 microliters (μl), 0.4 mmol] was added followed by the addition of 1,1'-carbonyldiimidazole (320 mg, 2.0 mmol). After stirring for 18 hours at room temperature in the absence of moisture, water (280 μl) was added and then the solvent evaporated in vacuo.

The resulting oil was dried by repeated in vacuo evaporation from dry dimethylformamide (4 times from 10 ml). The resulting phosphorimidazolidate was redissolved in 10 ml of dry dimethylformamide and added dropwise to a 0.4 mmol solution of the tri-n-octylamine salt of riboflavin-5'-monophosphate in 10 ml of dry dimethylformamide. The salt was prepared by adding a solution of the ammonium salt of riboflavin-5'-monophosphate (192 mg, 0.4 mmol) in 10 ml of water to a stirred solution of tri-n-octylamine (176 μl, 0.4 mmol) in 100 ml of acetone. After 30 minutes, the resulting mixture was evaporated in vacuo. The residue was dried by repeated evaporation in vacuo from dry dimethylformamide leaving the salt as an orange solid.

The above solution containing the phosphorimidazolidate of (6) and the riboflavin-5'-monophosphate salt was divided into two equal aliquots after 24 hours and one aliquot was evaporated in vacuo. The resulting residue was chromatographed on a column (2.5×78 cm) prepared from 100 g of Sephadex LH-20 (Pharmacia Fine Chemicals, Uppsala, Sweden) which had been preswollen (18 hours) in a 19:1 (v:v) mixture of dimethylformamide and triethylammonium bicarbonate (1 M, pH 7.5). The column was eluted with the above 19:1 (v:v) mixture and 10 ml fractions were collected. The effluent from the column was monitored by elution on silica gel 60 silanised RP-2 TLC places (E. Merck, Darmstadt, West Germany).

The TLC plates were developed using a 40:40:25:1:1 (v:v) mixture of acetone, chloroform, methyl alcohol, water, and triethylamine. Fractions numbered 11 through 17 from the above-mentioned column chromatography were combined and evaporated in vacuo. The residue was chromatographed on a column (2.5×75 cm) prepared from 125 g of Sephadex LH-20 which had been preswollen (18 hours) in 0.3 M ammonium bicarbonate. The column was eluted with 0.3 M ammonium bicarbonate collecting 10 ml fractions. The effluent was monitored by absorption of ultraviolet light at 254 nanometers (nm). The volume of the fractions was increased to 20 ml beginning with fraction number 150. The salt concentration of the eluent was decreased in a stepwise fashion as follows: 0.15 M ammonium bicarbonate at fraction number 295, 0.075 M ammonium bicarbonate at fraction number 376, and water at fraction number 430. A total of 480 fractions was collected. Fractions numbered 200 through 235 were combined and evaporated in vacuo leaving the labeled conjugate (7) as a yellow-orange residue. An alkaline, aqueous solution of this residue exhibited ultraviolet absorption maxima at the following wavelengths: 266 nm, 350 nm, 373 nm, and 450 nm. The yield, estimated from the absorption at 450 nm was about 5%.

A phosphodiesterase preparation (Worthington Biochemical Corp., Freehold, New Jersey USA) isolated from snake venom (*Crotalus Adamanteus*) hydrolyzed the above product to riboflavin-5'-monophosphate and the thyroxine substituted 5'-adenylic acid (6) wherein the trifluoacetyl blocking group had been removed.

1-II. BINDING ASSAY FOR THYROXINE

The above-prepared labeled conjugate was used in a prosthetic group-labeled specific binding assay as follows (further details regarding such an assay method may be found in the U.S. patent application Ser. No. 917,962 referred to hereinbefore):

A. Preparation of apoglucose oxidase

Purified glucose oxidase with low catalase activity obtained from the Research Products Division of Miles Laboratories, Inc., Elkhart, Indiana USA was twice dialyzed for 12 hours each against 0.5% (w:v) mannitol (30 volumes each). Aliquots of the dialyzate containing 100 mg of glucose oxidase each were lyophilized and stored at −20° C.

Bovine serum albumin (200 mg) was dissolved in 12 ml of water adjusted to pH 1.6 with concentrated sulfuric acid, mixed with 150 mg charcoal (RIA grade from Schwarz-Mann, Orangeburg, New York USA), and cooled to 0° C. Lyophilized glucose oxidase (100 mg) was redissolved in 3.1 ml of water and 3 ml was added to the stirred albumin-charcoal suspension with continued stirring for three minutes. The suspension was then filtered through a 0.8 micron, 25 millimeters (mm) diameter Millipore filter (Millipre Corp., Bedford, Massachusetts USA) mounted in a Sweenex filter apparatus (Millipore Corp.) on a 50 ml disposable plastic syringe. The filtrate was quickly neutralized to pH 7.0 by addition of 2 ml of 0.4 M phosphate buffer (pH 7.6) and thereafter 5 N sodium hydroxide. Dry charcoal (150 mg) was then added and stirred for one hour at 0° C. The resulting suspension was filtered first through a 0.8 micron Millipore filter and then through a 0.22 micron Millipore filter. To the filtrate was added glycerol to 25% (v:v) and the stabilized apoglucose oxidase preparation was stored at 4° C.

B. Assay Reagents

1. Labeled conjugate—The ethyl analog labeled conjugate prepared as in section 1-I above was diluted in 0.1 M phosphate buffer (pH 7) to a concentration of 1 micromolar ($\mu M$).

1. Apoenzyme—Apoglucose oxidase was diluted with 0.1 M phosphate buffer (pH 7) to a concentration of 0.6 $\mu M$ FAD binding sites. The FAD binding site concentration of the apoenzyme preparation was determined experimentally by measuring the minimum amount of FAD required to give maximum glucose oxidase activity when incubated with the apoenzyme.

3. Insolubilized antibody—A washed, moist cake of Sepharose 4B gel (Pharmacia Fine Chemicals, Uppsala, Sweden) activated by cyanogen bromide according to the method of March, et al, *Anal. Biochem.* 60:119 (1974) was added to a solution of 85 mg of antibody, (isolated from antiserum against a thyroxine-bovine serum albumin conjugate) in 20 ml of 0.1 M phosphate buffer (pH 7.0) and agitated slowly for 36 hours at 4° C. Upon completion of the coupling reaction, 1 ml of 1 M alanine was added and shaking continued for four more hours to block unreacted sites. The resulting Sepharose-bound antibody was washed on a scintered funnel with 400 ml each of 50 mM sodium acetate—500 millimolar (mM) sodium chloride (pH 5) and 50 mM phosphate buffer—500 mM sodium chloride (pH 7), and 800 ml of 100 mM phosphate buffer (pH 7). The moist filter cake was then suspended in 100 mM phosphate buffer (pH 7) containing 0.01% sodium azide to give 22 ml of an about 50% suspension.

4. Standard—A 1.15 mM stock solution of thyroxine in 5 mM sodium hydroxide was diluted to 2 $\mu M$ in 0.1 M phosphate buffer (pH 7).

5. Monitoring reagent—A glucose oxidase assay reagent was prepared to contain the following mixture per 130 $\mu l$: 25 $\mu l$ of 1.2 mg/ml peroxidase (Sigma Chemical Co., St. Louis, Missouri USA) in 0.1 M phosphate buffer (pH 7), 5 $\mu l$ of 10 mM 4-aminoantipyrine in water, 20 $\mu l$ of 25 mM 3,5-dichloro-2-hydroxybenzene sulfonate in 0.1 M phosphate buffer (pH 7), 30 $\mu l$ of 16.5% bovine serum albumin in 0.1 M phosphate buffer (pH 7), and 50 $\mu l$ of 1 M glucose in aqueous saturated benzoic acid solution.

C. Assay Procedure

Binding reaction mixtures were prepared by mixing 150 $\mu l$ of the insolubilized antibody suspension, 80 $\mu l$ of the labeled conjugate solution, various amounts of the standard thyroxine solution to give varying concentrations of thyroxine in the reaction mixtures, and a sufficient volume of 0.1 M phosphate buffer (pH 7) to make a total volume of 500 $\mu l$. The reaction mixtures were incubated with shaking for two hours at 25° C. Each reaction mixture was then vacuum filtered through a glass wool plugged, dry pasteur pipette previously treated sequentially with periodate and ethylene glycol solutions to eliminate possible FAD contamination. To a 300 $\mu l$ aliquot of each filtrate was added 130 $\mu l$ of the monitoring reagent and 50 $\mu l$ of the apoenzyme solution. After one hour, the adsorbance of each reaction mixture was measured at 520 nm.

D. Results

Following is Table 3 showing the results of the assay procedure in measuring thyroxine. The absorbance results are expressed as the average of duplicate runs corrected for residual enzyme activity in the apoenzyme solution (absorbance of 0.522) and for endogenous FAD in the antibody suspension (absorbance of 0.142).

TABLE 3

| Volume of Thyroxine Standard Added ($\mu l$) | Absorbance (520 nm) |
|---|---|
| 0 | 0.223 |
| 25 | 0.221 |
| 75 | 0.281 |
| 250 | 0.286 |

The results demonstrate that the present labeled conjugates are useful in a specific binding assay method for determining an iodothyronine.

2. Hexyl Analog

2-I. PREPARATION OF THE LABELED CONJUGATE 6-(6-Aminohexyl)amino-9-(2',3'-O-isopropylidene-$\beta$-D-ribofuranosyl) purine (2)

16.0 g (50 mmol) of 6-chloro-9-(2',3'-O-isopropylidene-$\beta$-D-ribofuranosyl) purine (1) [Hampton, et al, *J. Am. Chem. Soc.* 83:1501(1961)] was added with stirring to a molten (70° C.) sample of freshly distilled 1,6-diaminohexane (58 g, 500 mmol). The resulting mixture was stirred under argon at 40° C. for 18 hours. The excess diamine was removed by distillation under reduced pressure (60° C., 0.01 mm Hg). The resulting pale yellow residue was adsorbed onto 150 g of silica gel 60 (E. Merck, Darmstadt, West Germany) and used to top a chromatographic column prepared from a slurry of silica gel 60 (2 kg) in a 9:1 (v:v) mixture of absolute ethyl alcohol and triethylammonium bicarbonate (pH 7.5, 1 M). The column was eluted with the above 9:1 (v:v) solvent mixture and 900 20 ml fractions were collected. The fractions were examined by thin layer chromatography (TLC) on silica gel 60 eluting with a 7:3 (v:v)

mixture of absolute ethyl alcohol and triethylammonium bicarbonate (pH 7.5, 1 M). Fractions numbered 391 through 900 from the column chromatography were combined and evaporated in vacuo leaving 15.0 g of a glassy residue (74% yield). A 1 g sample of the glass was dissolved in a small volume of methyl alcohol which was then applied to the top of a column prepared from 80 g of Sephadex LH-20 (Pharmacia Fine Chemicals, Uppsala, Sweden) preswollen in methyl alcohol. The column was eluted with methyl alcohol. A total of ninety 8 ml fractions were collected. The fractions were examined by TLC on silica gel 60 eluting with a 7:3 (v:v) mixture of absolute ethyl alcohol and triethylammonium bicarbonate (pH 7.5, 1 M). Fractions numbered 19 through 27 from the column chromatography were combined and evaporated in vacuo leaving 910 mg (91% recovery) of a white glass.

Analysis: Calculated for $C_{19}H_{30}N_6O_4$: C, 56.14; H, 7.44; N, 20.68. Found: C, 53.91; H, 7.33; N, 19.18.

NMR (60 MHz, $CDCl_3$): δ 1.40 (s, 3H, isopropylidene), 1.63 (s, 3H, isopropylidene) 5.98 (d, 1H, 1'-ribose), 7.92 (s, 1H, purine), 8.36 (s, 1H, purine).

Optical Rotation $[\alpha]_D^{25} = -50.11°$ (c 1.0, methyl alcohol).

N-{6-[N-Trifluoroacetyl)-3,3',5,5'-tetraiodothyronyl]aminohexyl}-2',3'-O-isopropylidene adenosine (4)

A solution of 4.36 g (5.0 mmol) of α-(N-trifluoroacetyl) amino-β-[3,5-diiodo-4-(3',5'-diiodo-4'-hydroxyphenoxy)-phenyl]propanoic acid (3), prepared as described in section 1-I above, and 2.24 g (5.5 mmol) of 6-(6-aminohexyl)amino-9-(2',3'-O-isopropylidene-β-D-ribofuranosyl) purine (2) in 100 ml of dry dimethylformamide was prepared under a dry argon atmosphere at −20° C. To this cold stirred solution was added a solution of 1.52 g (5.5 mmol) of diphenylphosphoryl azide (Aldrich Chemical Co., Milwaukee, Wisconsin USA) in 50 ml of dry dimethylformamide followed by the addition of 0.8 ml (5.5 mmol) of dry triethylamine. The solution was left at room temperature for 22 hours. The solution was then added dropwise to 600 ml of cold (0° C.) water with stirring. The resulting white precipitate was collected by filtration and dried in vacuo (60° C.) to give 4.90 g (78% yield) of white solid. A sample of this solid was recrystallized from a mixture of acetone and water giving a white solid, m.p. 205°-207° C. (decomposed).

Analysis: Calculated for $C_{36}H_{38}F_3I_4N_7O_8$: C, 34.28; H, 3.04; N, 7.77. Found: C, 34.22; H, 2.99; N, 7.41.

Mass Spectrum (20 ma) m/e: 1262 [MH+], 1164 [M+ minus $COCF_3$].

Optical Rotation $[\alpha]_D^{25} = -21.89°$ (c 1.0, pyridine).

N-{6-[N-(Trifluoroacetyl)-3,3',5,5'-tetraiodothyronyl]aminohexyl}-2',3'-O-isopropylidene-5'-adenylic acid monotriethylamine salt monohydrate (5)

A solution of 1.89 g (1.5 mmol) of N-{6-N-(trifluoroacetyl)-3,3',5,5'-tetraiodothyronyl]aminohexyl}-2',3'-O-isopropylidene adenosine (4) in 15 ml of dry triethylphosphate was prepared under a dry argon atmosphere at −10° C. To the cold stirred solution was added 0.68 ml (7.5 mmol) of phosphorous oxychloride. The resulting solution was kept for 18 hours at −15° C. then added dropwise with stirring to 1.5 L of ice water. The resulting precipitate was collected by filtration and dried in vacuo to give 1.91 g (87% yield) of a white solid. The solid was dissolved in 10 ml methyl alcohol and 0.38 ml (2.6 mmol) of triethylamine was added. This solution was evaporated in vacuo and the resulting residue was recrystallized from a mixture of methyl alcohol and ethyl ether to give 720 mg (33% yield) of a white solid, m.p. 151°-154° C. (decomposed).

Analysis: Calculated for $C_{42}H_{56}F_3I_4N_8O_{12}P$: C, 34.54; H, 3.86; N, 7.67. Found: C, 35.24; H, 3.88; N, 7.75.

Mass Spectrum (20 ma) m/e: 1342 [MH+], 1244 [M+ minus $COCF_3$].

Optical Rotation $[\alpha]_D^{25} = -17.20°$ (c 1.0, $CH_3OH$).

N-{6-[N-(Trifluoroacetyl)-3,3',5,5'-tetraiodothyronyl]aminohexyl}-5'-adenylic acid (6)

600 mg (0.41 mmol) of N-{6-[N-(trifluoroacetyl)-3,3',5,5'-tetraiodothyronyl]aminohexyl}-2',3'-O-isopropylidene-5'-adenylic acid monotriethylamine salt monohydrate (5) was suspended in 0.6 ml of water (0° C.) and trifluoroacetic acid (6 ml) was added dropwise with stirring. After 50 minutes a clear solution was obtained. The solution was kept cold (0° C.) for an additional 15 hours then evaporated in vacuo (30° C.). The resulting residue was evaporated in vacuo five times from 20 ml volumes of anhydrous ethyl alcohol then triturated with 30 ml water and washed with a small volume of methyl alcohol. The resulting white solid (430 mg) was recrystallized from methyl alcohol to give 290 mg (54.6% yield) of white solid, m.p. 180°-183° C. (decomposed).

Analysis: Calculated for $C_{33}H_{35}F_3I_4N_7O_{11}P$: C, 30.46; H, 2.71; N, 7.54. Found: C, 30.77; H, 2.55; N, 7.29

Mass Spectrum (20 ma) m/e: 1302 [MH+], 1204 [M+ minus $COCF_3$].

Flavin adenine dinucleotide - thyroxine conjugate (7)

130.13 mg (0.1 mmol) of N-{6-[N-(trifluoroacetyl)-3,3',5,5'-tetraiodothyronyl]aminohexyl}-5'-adenylic acid (6) was placed in an argon atmosphere. To this sample was added a solution of 14 μl (0.1 mmol) of triethylamine in 1 ml of dry dimethylformamide followed by the addition of a solution of 16.2 mg (0.1 mmol) of 1,1'-carbonyldiimidazole in 1 ml of dry dimethylformamide. After 24 hours, a second equivalent of 1,1'-carbonyldiimidazole (16.2 mg) in 1 ml of dry dimethylformamide was added. The above reaction was allowed to proceed a total of 48 hours at room temperature excluding moisture. A sample of 47.3 mg (0.1 mmol) of the ammonium salt of riboflavin-5'-monophosphate was converted to the corresponding tri-n-octylamine salt as described in section 1-I above. This salt was dissolved in 3 ml of dry dimethylformamide and added to the above solution containing the phosphorimidazolidate of the adenylic acid intermediate (6).

The resulting solution was allowed to stand in the dark at room temperature excluding moisture for 24 hours. The solvent was evaporated in vacuo and the resulting residue was chromatographed on a column (2.5×78 cm) prepared from 100 g of Sephadex LH-20 (Pharmacia Fine Chemicals, Uppsala, Sweden) which had been preswollen (18 hours) in a 19:1 (v:v) mixture of dimethylformamide and triethylammonium bicarbonate (1 M, pH 7.5). The column was eluted with the above 19:1 (v:v) mixture and 5 ml fractions were collected. The effluent from the column was monitored by elution on silica gel 60 silanised RP-2 TLC plates (E. Merck, Darmstadt, West Germany). The TLC plates were developed using a 40:40:25:1:1 (v:v) mixture of acetone, chloroform, methyl alcohol, water, and triethylamine.

Fractions numbered 24 through 38 from the column chromatography were combined and evaporated in vacuo. The residue was chromatographed on a column (2.5×85 cm) prepared from 125 g of Sephadex LH-20 which had been preswollen (18 hours) in 0.1 M ammonium bicarbonate. The column was eluted with a linear gradient generated from 2 L of 0.1 M ammonium bicarbonate and 2 L of water and 23 ml fractions collected. The effluent was monitored by ultraviolet absorption (254 nm). Fractions numbered 170 through 182 were combined and evaporated in vacuo. The residue was chromatographed on a column (2.5×55 cm) prepared from 80 g of Sephadex LH-20 which had been preswollen in 0.05 M ammonium bicarbonate. The column was eluted with a linear gradient generated from 2 L of 0.05 M ammonium bicarbonate and 2 L of 0.02 M ammonium bicarbonate. The effluent was monitored by ultraviolet absorption (254 nm). Elution was continued with 2 L of 0.2 M ammonium bicarbonate, collecting 23 ml fractions. A total of 257 fractions was collected. Fractions numbered 70 through 110 were combined and evaporated in vacuo leaving the labeled conjugate (7) as a yellow-orange residue. An alkaline, aqueous solution of this residue exhibited ultraviolet absorption maxima at the following wavelengths: 270 nm, 345 nm, and 450 nm. The yield, estimated from the absorption at 450 nm, was about 5%.

A phosphodiesterase preparation (Worthington Biochemical Corp., Freehold, New Jersey USA) isolated from snake venom (*Crotalus Adamanteus*) hydrolyzed the above product to riboflavin-5'-monophosphate and the thyroxine substituted 5'-adenylic acid (6) wherein the trifluoroacetyl blocking group had been removed.

2-II. BINDING ASSAY FOR THYROXINE

The above-prepared labeled conjugate was used in a prosthetic-group labeled specific binding assay as follows (further details regarding such an assay method may be found in the U.S. patent application Ser. No. 917,961 referred to hereinbefore):

A. Preparation of apoglucose oxidase

The apoenzyme used was prepared by the method described in section 1-II, part A above.

B. Assay Reagents

1. Labeled conjugate—The hexyl analog labeled conjugate prepared as in section 2-I above was diluted in 0.1 M phosphate buffer (pH 7) to a concentration of 100 nM.
2. Apoenzyme—This reagent was the same as that described in section 1-II, part B-2 above.
3. Insolubilized antibody—This reagent was the same as that described in section 1-II, part B-3 above.
4. Standard—A 1.15 mM stock solution of thyroxine in 5 mM sodium hydroxide was diluted to 1 μM in 0.1 M phosphate buffer (pH 7).
5. Monitoring reagent—A glucose oxidase reagent was prepared to contain the following mixture per 117 μl: 25 μl of 1.2 mg/ml peroxidase (Sigma Chemical Co., St. Louis, Missouri USA) in 0.1 M phosphate buffer (pH 7), 5 μl of 10 mM 4-aminoantipyrine in water, 20 μl of 25 mM 3,5-dichloro-2-hydroxybenzene sulfonate in 0.1 M phosphate buffer (pH 7), 17 μl of 30% bovine serum albumin in 0.1 M phosphate buffer (pH 7), and 50 μl of 1 M glucose in aqueous saturated benzoic acid solution.

C. Assay Procedure

Binding reaction mixtures were prepared by mixing 30 μl of the insolubilized antibody suspension, 100 μl of the labeled conjugate solution, either 100 μl or none of the standard thyroxine solution, and a sufficient volume of 0.1 M phosphate buffer (pH 7) to make a total volume of 500 μl. The reaction mixtures were incubated with shaking for two hours at 25° C. Each reaction mixture was then vacuum filtered through a glass wool plugged, dry pasteur pipette previously treated sequentially with periodate and ethylene glycol solutions to eliminate possible FAD contamination. To a 350 μl aliquot of each filtrate was added 117 μl of the monitoring reagent and 50 μl of the apoenzyme solution. After one hour, the absorbance of each reaction mixture was measured at 520 nm.

D. Results

Following is Table 4 showing the results of the assay procedure in measuring thyroxine. The absorbance results are expressed as the average of duplicate runs corrected for residual enzyme activity in the apoenzyme solution (absorbance of 0.467) and for endogenous FAD in the antibody suspension (absorbance of 0.041).

TABLE 4

| Volume of Thyroxine Standard Added (μl) | Absorbance (520 nm) |
|---|---|
| 0 | 0.231 |
| 100 | 0.295 |

The results demonstrate that the present labeled conjugates are useful in a specific binding assay method for determining an iodothyronine.

What is claimed is:

1. A compound of the formula:

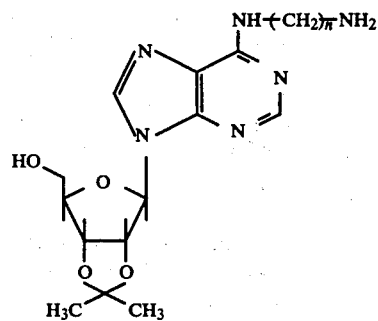

wherein n=2, through 6.

2. The compound of claim 1 wherein n=2.
3. The compound of claim 1 wherein n=6.

* * * * *